United States Patent
Tanaka

(10) Patent No.: US 11,299,454 B2
(45) Date of Patent: Apr. 12, 2022

(54) METHOD OF PRODUCING N-VINYLCARBOXYLIC ACID AMIDE

(71) Applicant: SHOWA DENKO K.K., Tokyo (JP)

(72) Inventor: Naoyuki Tanaka, Kawasaki (JP)

(73) Assignee: SHOWA DENKO K.K., Tokyo (JP)

( * ) Notice: Subject to any disclaimer, the term of this patent is extended or adjusted under 35 U.S.C. 154(b) by 833 days.

(21) Appl. No.: 15/999,787

(22) PCT Filed: Jan. 16, 2017

(86) PCT No.: PCT/JP2017/001214
§ 371 (c)(1),
(2) Date: Aug. 20, 2018

(87) PCT Pub. No.: WO2017/145569
PCT Pub. Date: Aug. 31, 2017

(65) Prior Publication Data
US 2021/0214302 A1    Jul. 15, 2021

(30) Foreign Application Priority Data

Feb. 22, 2016 (JP) .............................. JP2016-031378

(51) Int. Cl.
| | |
|---|---|
| *C07C 231/12* | (2006.01) |
| *C07C 231/24* | (2006.01) |
| *C07C 233/18* | (2006.01) |
| *B01J 21/04* | (2006.01) |
| *B01J 23/42* | (2006.01) |

(52) U.S. Cl.
CPC ............ *C07C 231/12* (2013.01); *B01J 21/04* (2013.01); *B01J 23/42* (2013.01); *C07C 231/24* (2013.01); *C07C 233/18* (2013.01)

(58) Field of Classification Search
CPC ... C07C 231/12; C07C 231/24; C07C 233/18; C07C 233/05

USPC ......................................................... 564/123
See application file for complete search history.

(56) References Cited

U.S. PATENT DOCUMENTS

| | | |
|---|---|---|
| 4,401,516 A | 8/1983 | Matzinger |
| 5,723,665 A | 3/1998 | Kato et al. |
| 6,072,084 A | 6/2000 | Aizawa et al. |

FOREIGN PATENT DOCUMENTS

| | | |
|---|---|---|
| CN | 1073551 C | 10/2001 |
| JP | 61-289069 A | 12/1986 |
| JP | 63-132868 A | 6/1988 |
| JP | 02-188560 A | 7/1990 |
| JP | 06-287232 A | 10/1994 |
| JP | 07-097358 A | 4/1995 |
| JP | 08-081428 A | 3/1996 |
| JP | 2002-167369 A | 6/2002 |

OTHER PUBLICATIONS

Office Action for corresponding TW 106101426, dated Jan. 12, 2018.
International Search Report for PCT/JP2017/001214, dated Mar. 14, 2017.
Communication dated Aug. 10, 2020, from The China National Intellectual Property Administration in Application No. 201780011463.X.

*Primary Examiner* — Ana Z Muresan
(74) *Attorney, Agent, or Firm* — Sughrue Mion, PLLC

(57) ABSTRACT

A method for producing an N-vinylcarboxylic acid amide is provided, the method focusing on unsaturated aldehydes that are contained as impurities generated during a reaction. The method for producing an N-vinylcarboxylic acid amide includes a step for controlling the contained amount of unsaturated aldehydes in the N-vinylcarboxylic acid amide to be not more than 20 mass ppm.

5 Claims, 1 Drawing Sheet

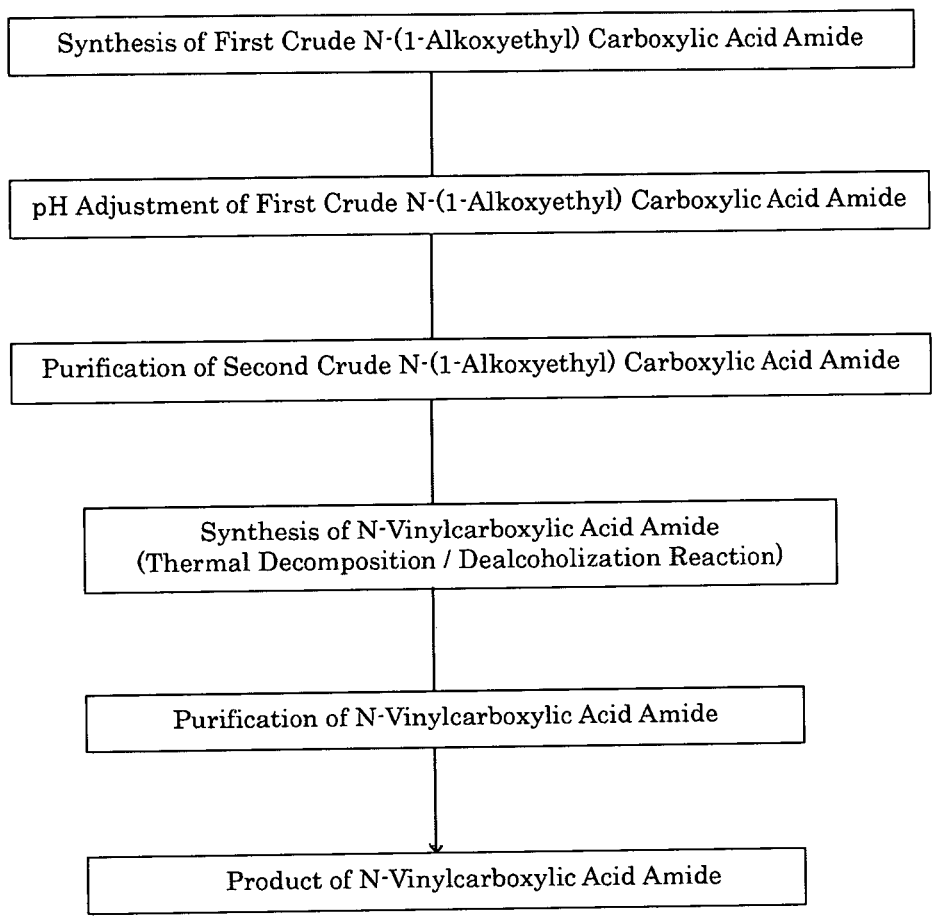

METHOD OF PRODUCING N-VINYLCARBOXYLIC ACID AMIDE

This Application is a National Stage of International Application No. PCT/JP2017/001214 filed Jan. 16, 2017, claiming priority based on Japanese Patent Application No. 2016-031378 filed Feb. 22, 2016.

TECHNICAL FIELD

The present invention relates to a method of producing N-vinylcarboxylic acid amide which is an industrially useful monomer for use in the production of N-vinylcarboxylic acid amide-based polymers for use in flocculants, liquid absorbents, thickeners, and the like.

This application claims priority right based on Japanese Patent Application No. 2016-031378 filed in Japan on Feb. 22, 2016, the content of which is incorporated herein by reference.

BACKGROUND ART

Many methods for producing N-vinylcarboxylic acid amide have been proposed. For example, there is a known method including steps of producing N-(1-alkoxyethyl)carboxylic acid amide as an intermediate from carboxylic acid amide, acetaldehyde and alcohol; and synthesizing N-vinylcarboxylic acid amide by thermal decomposing or catalytic decomposing the N-(1-alkoxyethyl) carboxylic acid amide. Further, there is another known method including steps of synthesizing ethylidene bis-carboxylic acid amide from a carboxylic acid amide and acetaldehyde and decomposing ethylidene bis-carboxylic acid amides to N-vinylcarboxamide and carboxylic acid amide.

Generally, a polymerizability of a monomer depends on an amount of a polymerization inhibitor contained in it as an impurity. In general, the polymerization inhibitor is removed by various methods in order to lower the amount to an allowable concentration or lower.

From this viewpoint, an N-vinylcarboxylic acid amide synthesized by thermal decomposition or catalytic decomposition described above is purified by a method such as distillation, extraction, recrystallization, or the like to increase purity of the N-vinylcarboxylic acid amide, so as to improve its polymerizability. As disclosed purification methods, Patent Document 1 discloses an extraction method by using water and an aromatic hydrocarbon. Patent Document 2 discloses a method of cooling crystallization from a mixed organic solvent. Patent Document 3 discloses an extraction method by using an aqueous solution of an inorganic salt and an aromatic hydrocarbon. Patent Document 4 discloses a method of extractive distillation using polyhydric alcohol. However, in any one of the above methods, as a monomer for stably obtaining a high-molecular-weight polymer usable as a flocculant, a liquid absorbent, a thickener or the like, a polymerizable N-vinylcarboxylic acid amide is difficult to be produced.

Patent Document 5 discloses that it is necessary to reduce an amount of N-1,3-butadienylcarboxylic acid amide in N-vinylcarboxylic acid amide to be used, in order to synthesize an N-vinylcarboxylic acid amide-based polymer having a high molecular weight. Patent Document 5 further discloses that it is clearly demonstrated that N-vinylcarboxamide having an amount of N-1,3-butadienylcarboxylic acid amide of 30 mass ppm or less is highly polymerizable.

Document 5 also discloses a specified purification treatment method for reducing the amount of N-1,3-butadienylcarboxylic acid amide.

[Patent Document 1] Japanese Unexamined Patent Publication No. 61-289069
[Patent Document 2] Japanese Unexamined Patent Publication No. 63-132868
[Patent Document 3] Japanese Unexamined Patent Publication No. 2-188560
[Patent Document 4] U.S. Pat. No. 4,401,516
[Patent Document 5] Japanese Unexamined Patent Publication No. 8-81428

SUMMARY OF THE INVENTION

However, even using N-vinylcarboxylic acid amide having a reduced amount of N-1,3-butadienylcarboxylic acid amide, the polymerizability is not satisfactory due to the presence of some polymerization inhibiting substances.

The inventors of the present invention conducted intensive studies and found that with respect to the polymerizability of N-vinylcarboxylic acid amide, in addition to N-1,3-butadienylcarboxylic acid amide, an unsaturated aldehyde is also involved in inhibiting the polymerizable of N-vinylcarboxylic acid amide. Further, the inventor found that in the method of producing an N-vinylcarboxylic acid amide by using an N-(1-alkoxyethyl) carboxylic acid amide as an intermediate, the amount of the unsaturated aldehyde mixed in the final N-vinylcarboxylic acid amide can be reduced by adjusting a pH of the crude N-vinylcarboxylic acid amide before the distillation.

That is, the present invention includes the following items.

[1] A method of producing N-vinylcarboxylic acid amide, comprising: a step of controlling an amount of unsaturated aldehydes in N-vinylcarboxylic acid amide to 20 mass ppm or less.

[2] The method of producing N-vinylcarboxylic acid amide according to [1], further comprising: a step of obtaining N-vinylcarboxylic acid amide by using the de-alcoholization reaction from N-(1-alkoxyethyl) carboxylic acid amide,
wherein the step of controlling an amount of unsaturated aldehydes comprises steps of:
obtaining a second crude N-(1-alkoxyethyl) carboxylic acid amide by adjusting a pH of a first crude N-(1-alkoxyethyl) carboxylic acid amide to 8.0 to 8.5; and purifying the N-(1-alkoxyethyl) carboxylic acid amide by distilling the second crude N-(1-alkoxyethyl) carboxylic acid amide.

[3] The method of producing N-vinylcarboxylic acid amide according to [2], further comprising: a step of producing the N-(1-alkoxyethyl) carboxylic acid amide from carboxylic acid amide, acetaldehyde and alcohol; or from carboxylic acid amide and acetaldehyde dialkyl acetal.

[4] The method of producing N-vinylcarboxylic acid amide according to any one of [1] to [3], wherein the N-vinylcarboxylic acid amide is a N-vinylacetamide.

[5] The method of producing N-vinylcarboxylic acid amide according to any one of [2] to [4],
wherein the pH adjustment of the first crude N-(1-alkoxyethyl) carboxylic acid amide before the distillation purification step is carried out by using 30 to 48% by mass of one selected from the group consisting of a sodium hydroxide aqueous solution and a potassium hydroxide aqueous solution.

[6] The method of producing N-vinylcarboxylic acid amide according to any one of [1] to [5], wherein the unsaturated aldehydes comprises at least one selected from the group consisting of crotonaldehyde, 2-ethyl-2-butenal, 2-methyl-2-pentenal, 2-hexenal, 2,4-hexadienal, 2,4-octadienal, 2,4,6-octatrienal, and trans-2-octenal, and an amount of the unsaturated aldehyde is a total amount of crotonaldehyde, 2-ethyl-2-butenal, 2-methyl-2-pentenal, 2-hexenal, 2,4-hexadienal, 2, 4-octadienal, 2,4,6-octatrienal and trans-2-octenal.

According to the present invention, N-vinylcarboxylic acid amide having high polymerizability can be produced.

BRIEF DESCRIPTION OF THE DRAWINGS

FIG. 1 is a production flow of N-vinylcarboxylic acid amide.

DETAILED DESCRIPTION OF THE INVENTION (Production Method of N-Vinylcarboxylic Acid Amide)

The method of producing N-vinylcarboxylic acid amide of the present invention includes a step of controlling an amount of unsaturated aldehydes in N-vinylcarboxylic acid amide to 20 mass ppm or less. The method of producing an N-vinylcarboxylic acid amide of the present invention may include a step of obtaining an N-vinylcarboxylic acid amide from an N-(1-alkoxyethyl) carboxylic acid amide by using a de-alcoholization reaction. The method may include steps of obtaining a second crude N-(1-alkoxyethyl) carboxylic acid amide by adjusting the pH of a first crude N-(1-alkoxyethyl) carboxylic acid amide to 8.0 to 8.5; and purifying the N-(1-alkoxyethyl) carboxylic acid amide by distilling the second crude N-(1-alkoxyethyl) carboxylic acid amide.

The overall process of producing N-vinylcarboxylic acid amide disclosed in one embodiment of the present invention is shown in FIG. 1.

An example of this embodiment will be described in more detail below.

A crude N-(1-alkoxyethyl)carboxylic acid amide containing a N-(1-alkoxyethyl)carboxylic acid which is produced by a reaction is adjusted to a pH of 8.0 to 8.5, for example, by addition of alkali. In this state, the crude N-(1-alkoxyethyl)carboxylic acid amide is purified by distillation. The N-(1-alkoxyethyl)carboxylic acid amide is then de-alcoholized by thermal decomposition reaction to yield a crude N-vinylcarboxylic acid amide. The crude N-vinylcarboxylic acid amide is purified mainly by crystallization to yield the desired N-vinylcarboxylic acid amide.

The reaction formulas are shown below.

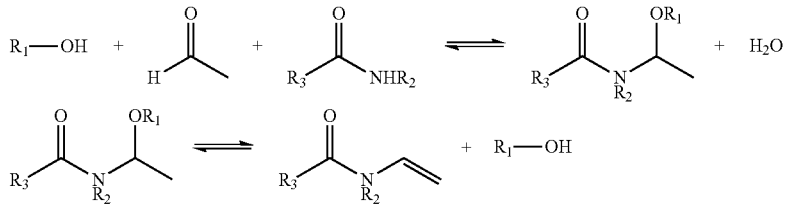

(In the formula, $R_1$ represents an alkyl group having 1 to 5 carbon atoms, $R_2$ independently represents a hydrogen atom or an alkyl group having 1 to 5 carbon atoms, and $R_3$ represents an alkyl group having 1 to 5 carbon atoms.)

In the crude N-(1-alkoxyethyl) carboxylic acid amide, equilibrium reactions shown in Reactions (a) to (d) occur, and as a result, various impurities are generated. When distillation purification of the N-(1-alkoxyethyl) carboxylic acid amide is carried out without adjusting the pH prior to the distillation, the crude N-(1-alkoxyethyl) carboxylic acid amide containing N-(1-alkoxyethyl) carboxylic acid amide will be heated and distilled under an acidic condition. As a result, most of the N-(1-alkoxyethyl) carboxylic acid amide is decomposed and a good yield cannot be obtained.

Therefore, the pH is adjusted to 8.0 to 8.5 by using alkali. The pH here is a value at 25° C.

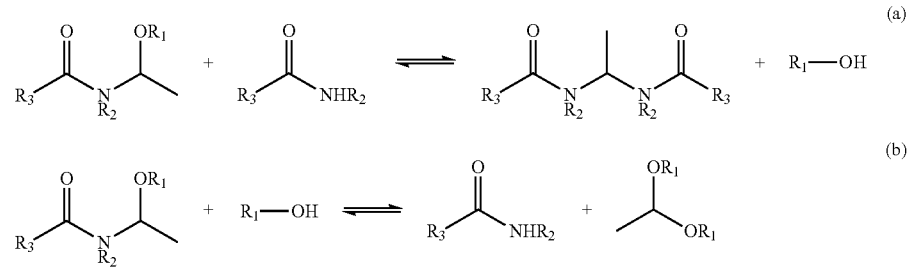

-continued

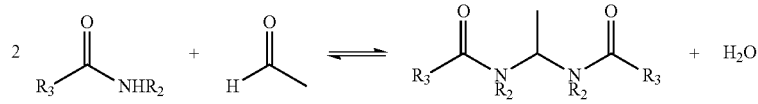
(c)

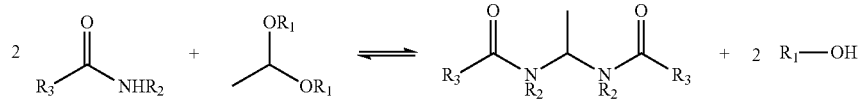
(d)

When the pH at this time is less than 8.0, since the crude N-(1-alkoxyethyl)carboxylic acid amide is heated under a pH of less than 8.0, Reaction (a) is shifted to the right progress and the carboxylic acid amide decreases. Then, in Reaction (b), the carboxylic acid amide is formed from N-(1-alkoxyethyl) carboxylic acid amide and alcohol by an equilibrium reaction. In Reaction (c), a reaction between carboxylic acid amide and aldehyde occurs, or in Reaction (d), a reaction between the carboxylic acid amide and acetaldehyde dialkyl acetal occurs. The Reactions (b) and (c) produce ethylidenebiscarboxylic acid amide. As a result, recovery of N-(1-alkoxyethyl) carboxylic acid amide becomes difficult. Although the above Reactions (a), (c) and (d) are all equilibrium reactions, since the ethylidenebiscarboxylic acid amide precipitates because solubility of ethylidenebiscarboxylic acid amide is smaller than other reactive substrates, the equilibrium reactions proceed to the right progress. Therefore, the decomposition of N-(1-alkoxyethyl) carboxylic acid amide is accelerated.

On the other hand, when the pH exceeds 8.5, by heating in distillation step, since an aldol condensation reaction (e) of the raw material acetaldehyde occurs, an amount of the aldol which is a precursor of an unsaturated aldehyde and an amount of unsaturated aldehyde increases. The aldol condensation reaction (e) is shown below.

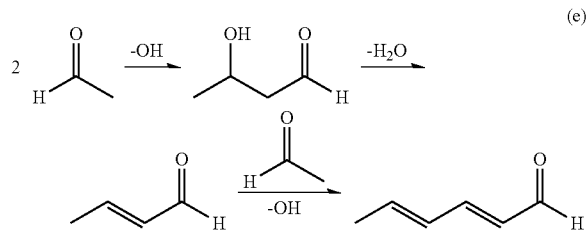
(e)

Here, the increased unsaturated aldehyde includes, for example, crotonaldehyde, 2-ethyl-2-butenal, 2-methyl-2-pentenal, 2-hexenal, 2,4-hexadienal, 2,4-octadienal, 2,4,6-octatrienal, trans-2-octenal and the like. Even a small amount of these unsaturated aldehydes may lower polymerizability of the N-vinylcarboxylic acid amide. Even if the pH is adjusted to 8.0 to 8.5, the aldol condensation reaction proceeds slightly and a small amount of aldol and unsaturated aldehyde are produced. However, when the crude N-(1-alkoxyethyl) carboxylic acid amide is distilled and purified in the state of pH 8.0 to 8.5, its amount does not change before or after distillation purification. It is possible to reduce the amount of aldol and unsaturated aldehyde mixed in the N-(1-alkoxyethyl)carboxylic acid amide fraction. When N-(1-alkoxyethyl)carboxylic acid amide is purified in a state of pH more than 8.5, since the aldol condensation reaction is accelerated by heating during distillation as described above, the absolute amount of aldol and unsaturated aldehyde increases. Further, in the distillation purification, these components have a higher boiling point than alcohols and acetaldehydes contained in the crude N-(1-alkoxyethyl) carboxylic acid amide, and as a result, the amount of the aldol and unsaturated aldehyde mixed in the purified N-(1-alkoxyethyl) increases. A fraction of aldol and unsaturated aldehydes mixed in this purified N-(1-alkoxyethyl) carboxylic acid amide is reduced in the subsequent steps (thermal decomposition step, selective hydrogenation step), and finally in the crystallization step most of them are removed. However, since there is a distribution to the crystal (10 to 50% of aldol and unsaturated aldehydes in the crystallization raw material is distributed to the crystal), it is difficult to completely separate them. For this reason, a low concentration of unsaturated aldehyde will be mixed in the N-vinylcarboxylic acid amide. This is the reason why it is effective to adjust the pH of the crude N-(1-alkoxyethyl) carboxylic acid amide prior to the distillation of N-(1-alkoxyethyl) carboxylic acid amide.

From the above, the crude N-(1-alkoxyethyl) carboxylic acid amide is subjected to the distillation step after adjusting the pH to 8.0 to 8.5 before the distillation step.

<Unsaturated Aldehydes and their Amounts>

Examples of the unsaturated aldehydes include crotonaldehyde, 2-ethyl-2-butenal, 2-methyl-2-pentenal, 2-hexenal, 2,4-hexadienal, 2,4-octadienal, 2,4,6-octatrienal, trans-2-octenal and the like.

Analysis of unsaturated aldehydes may be carried out by either GC method or HPLC method. The amount of unsaturated aldehydes is the total amount of each unsaturated aldehyde, such as crotonaldehyde, 2-ethyl-2-butenal, 2-methyl-2-pentenal, 2-hexenal, 2,4-hexadienal, 2,4-octadienal, 2,4,6-octatrienal, trans-2-octenal and the like. However, the detection limit of various unsaturated aldehydes is required to be quantitative at a concentration of 5 mass ppm or less.

As a measurement method, a gas chromatography method (GC method) or a high performance liquid column chromatography method (HPLC method) may be used.

As the GC method, measurement conditions are shown as following.

Apparatus: SHIMADZU GC-2014 (FID)
Column: HP-WAX φ 0.25 mm×30 m
Flow rate: He 1 ccm
Spirit ratio: 40
Column temperature: 40° C. (7 min)→temperature increase (25° C./min)→130° C. (15 min)→4 temperature increase (30° C./min)→220° C. (2 min)
Injection temperature: 200° C.
Detector: Hydrogen Flame Ionization Detector (FID) 230° C.

As the HPLC method, measurement conditions are shown as following.

Column: Shodex SIL-5B
Flow rate: 1.0 mL/min
Column temperature: 40° C.
Eluent: isopropyl alcohol (IPA)/n-hexane=1/9(mass ratio)
Detector: UV <N-(1-Alkoxyethyl) Carboxylic Acid Amide>

The N-(1-alkoxyethyl) carboxylic acid amide used in the present invention is preferably a compound represented by the following general formula (I):

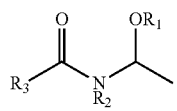

(I)

wherein $R_1$ represents an alkyl group having 1 to 5 carbon atoms, $R_2$ independently represents a hydrogen atom or an alkyl group having 1 to 5 carbon atoms, and $R_3$ represents an alkyl group having 1 to 5 carbon atoms.

Examples thereof include N-(1-methoxyethyl)acetamide, N-(1-methoxyethyl)-N-methylacetamide, N-(1-ethoxyethyl)acetamide, N-(1-ethoxyethyl)-N-methylacetamide, N-(1-propoxyethyl)acetamide, N-(1-isopropoxyethyl)acetamide, N-(1-butoxyethyl)acetamide, N-(1-isobutoxyethyl)acetamide, N-(1-methoxyethyl)propionamide, N-(1-ethoxyethyl)propionamide, N-(1-propoxyethyl)propionamide, N-(1-isopropoxyethyl)propionamide, N-(1-butoxyethyl)propionamide, N-(1-isobutoxyethyl)propionamide, N-(1-methoxyethyl)isobutyramide, N-(1-ethoxyethyl)isobutyramide N-(1-propoxyethyl)isobutyramide, N-(1-isopropoxyethyl)isobutyramide, N-(1-butoxyethyl)isobutyramide, N-(1-isobutoxyethyl)isobutyramide and the like. N-(1-methoxyethyl)acetamide, N-(1-isopropoxyethyl)acetamide, and N-(1-methoxyethyl)isobutyramide are preferable, and N-(1-methoxyethyl)acetamide is more preferable.

<N-Vinylcarboxylic Acid Amide>

The N-vinylcarboxylic acid amide obtained by the production method of the present invention corresponds to the aforementioned N-(1-alkoxyethyl) carboxylic acid amide. The N-vinylcarboxylic acid amide is preferably a compound represented by the following general formula (H):

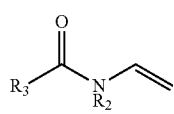

(II)

wherein $R_2$ and $R_3$ have the same meanings as defined above.

Examples of N-vinylcarboxylic acid amides includes N-vinylacetamide, N-methyl-N-vinylacetamide, N-vinylpropionamide, N-methyl-N-vinylpropionamide, N-vinylisobutyramide and N-methyl-N-vinylisobutyramide. And N-vinylacetamide is preferable.

<Synthesis of First Crude N-(1-Alkoxyethyl)Carboxylic Acid Amide>

No particular limitation is imposed on the method of synthesizing the N-(1-alkoxyethyl)carboxylic acid amide used in the present invention or a solution containing it, but examples of the method include a method of synthesizing N-(1-alkoxyethyl) carboxylic acid amide by using a carboxylic acid amide, acetaldehyde and an alcohol, and a method of synthesizing N-(1-alkoxyethyl) carboxylic acid amide by using a carboxylic acid amide and an acetaldehyde dialkyl acetal in the presence of an acid catalyst, and the like.

<pH Adjustment of First Crude N-(1-Alkoxyethyl) Carboxylic Acid Amide>

An alkali is added to the obtained first crude N-(1-alkoxyethyl) carboxylic acid amide to adjust the pH to 8.0 to 8.5 and to obtain a second crude N-(1-alkoxyethyl) carboxylic acid amide.

Here, the pH is measured at 20 to 25° C. using a personal pH meter YOKOGAWA PH 71 as a measuring instrument.

The alkali used for adjusting the pH of the first crude N-(1-alkoxyethyl) carboxylic acid amide is preferably a strong alkali such as sodium hydroxide or potassium hydroxide. From the viewpoints of easy availability and economic efficiency, sodium hydroxide is more preferable. As the alkali, an aqueous solution of 1 to 48 mass % which is commercially available as an aqueous solution may be used, or a solid one (100%) may be used. Water is also added at the same time due to the addition of the aqueous alkali solution. However, when the water amount is high, the equilibrium reaction between N-(1-alkoxyethyl)carboxylic acid amide and a raw material of acetaldehyde, alcohol and carboxylic acid amide is shifted and the yield of N-(1-alkoxyethyl)carboxylic acid amide decreases. On the other hand, when a solid alkali is used, it is difficult to adjust the pH due to dissolution delay of the solid. From the above, the concentration of the alkaline aqueous solution to be added is preferably from 30 to 48% by mass, and more preferably 48% by mass.

<Purification of Second Crude N-(1-Alkoxyethyl)Carboxylic Acid Amide>

The method of separating and purifying the second crude N-(1-alkoxyethyl)carboxylic acid amide includes a distillation method, which is the most preferable method in view of economy and efficiency. Examples of the distillation method include a single distillation method and a precision distillation method in which a distillation apparatus is equipped with a rectification column. There is no particular limitation on the apparatus for performing the single distillation method, but as a countermeasure for suppressing an increase of an amount of a metal component in the distillate, which is introduced by accompanying the mist, it is effective to install a mist separator in the gas line. In addition, when setting the distillation conditions, it is necessary to sufficiently consider deterioration. Since N-(1-alkoxyethyl) carboxylic acid amide is easy to deteriorate by heat, distillation at the lowest possible temperature is preferred. Therefore, the distillation is suitable to be performed under a reduced pressure of 10 kPaA or less.

<Synthesis of N-Vinylcarboxylic Acid Amide (Thermal Decomposition/De-Alcoholization Reaction)>

Converting the purified N-(1-alkoxyethyl) carboxylic acid amide to N-vinylcarboxylic acid amide by thermal decomposition and catalytic decomposition are carried out by a known method. These conditions include, for example, in gas phase or liquid phase, at a reaction temperature of from 60 to 600° C., for a reaction time of from 0.3 seconds to 2 hours, and under an operating pressure of from 0.1 kPaA to atmospheric pressure. It is preferable to carry out the thermal decomposition reaction in a gas phase at a reaction temperature of 300 to 600° C., for a reaction time of 0.3 seconds to 1 minute, and under a pressure of 10 to 30 kPaA without a catalyst.

<Purification of N-Vinylcarboxylic Acid Amide>

When N-(1-alkoxyethyl) carboxylic acid amide is thermally decomposed or catalytically decomposed and is converted to N-vinylcarboxylic acid amide, N-1,3-butadienylcarboxylic acid amide is produced as a byproduct.

As a method of reducing and removing N-1,3-butadienylcarboxylic acid amide from N-vinylcarboxylic acid amide, there is no particular limitation thereon as long as it is a physical method in which 1,3-butadienylcarboxylic acid amide and N-vinylcarboxylic acid amide are easily separated; or as long as it is a chemical method in which N-1,3-butadienylcarboxylic acid amide is converted. Embodiments of the purification treatment methods include, for example, a physical purification treatment method such as a precision distillation method, a recrystallization method, a pressure crystallization method, a treatment method with an activated carbon adsorbent, and the like, in which N-vinylcarboxylic acid amide or a solution thereof is treated; and a chemical purification treatment method, such as a method of treating benzoquinone or the like with a Diels-Alder reaction, a method of treating a 1,3-butadienyl group by a selective hydrogenation reaction, and the like, in which N-1,3-butadienylcarboxylic acid amide is converted. Each method can be performed singly or in combination.

The N-vinylcarboxylic acid amide is suitably purified by crystallization. For the crystallization method using a crystallizer, either a batch type or a continuous type may be used, and there is no strict condition for the structure of the apparatus. As a crystallizer, a batch type crystallizer, a D. T. B. type crystallizer, a Krystal-Oslo type crystallizer, a M. W. B. type crystallizer, a B. M. C. type crystallizer, a pressure crystallizer, and the like may be used. Examples of the solvent in the case of using a recrystallization solvent include aromatic hydrocarbons such as toluene, xylene, and the like; aliphatic hydrocarbons such as hexane, cyclohexane, pentane, heptane, and the like; alcohols such as methanol, ethanol, n-propyl alcohol, isopropyl alcohol, isobutanol, and the like; halogenated hydrocarbons such as methylene chloride, chloroform, and the like; ketones such as acetone, methyl ethyl ketone, and the like; esters such as methyl acetate, ethyl acetate, propyl acetate, and the like; ethers such as diethyl ether, and the like. Methanol, isopropyl alcohol, toluene and cyclohexane are particularly preferred. In addition, these solvents may be used in combination.

<Polymerizability of N-Vinylcarboxylic Acid Amide>

According to the present invention, N-vinylcarboxylic acid amide having high polymerizability can be obtained. Since the N-vinylcarboxylic acid amide according to the present invention has high polymerizability, a polymer having a high degree of polymerization can be obtained in a short amount of time. In the present invention, the polymerizability is evaluated by measuring the standard arrival time of a temperature peak from the addition of the polymerization initiator. Detailed procedures are described in the examples. The N-vinylcarboxylic acid amide of the present invention reaches the standard temperature in a short amount of time.

EXAMPLE

Hereinafter, the present invention will be described in detail with reference to Examples, but it should not be construed as limiting the technical scope of the present invention.

Example 1

(Production of N-Vinylacetamide)

<Synthesis of First Crude N-(1-Methoxyethyl)Acetamide>

298 g of acetaldehyde, 651 g of methanol and 100 g of acetamide were reacted under presence of a sulfuric acid catalyst to obtain a first crude N-(1-methoxyethyl)acetamide having a pH of 1.6.

<pH Adjustment of First Crude N-(1-Methoxyethyl)Acetamide>

A 48% by mass aqueous sodium hydroxide solution was added to the obtained first crude N-(1-methoxyethyl)acetamide to adjust the pH to 8.0, and then the second crude N-(1-methoxyethyl)acetamide was obtained.

The aldol concentration in the second crude N-(1-methoxyethyl)acetamide after adjustment of the pH was 1200 ppm by mass and the concentration of the unsaturated aldehyde was 170 ppm by mass, as shown in Table 1.

<Distillation of Second Crude N-(1-Methoxyethyl)Acetamide>

Distillation of the second crude N-(1-methoxyethyl)acetamide was carried out under conditions of a bottom temperature of 100° C., a degree of vacuum of 0.27 kPaA, by using a simple distillation apparatus. An N-(1-methoxyethyl)acetamide having a purity of 92% by mass was obtained. No increase in an amount of aldol and unsaturated aldehydes was observed in the distillation operation.

<Synthesis of N-Vinylacetamide (Thermal Decomposition and De-Alcoholization)>

The Purified N-(1-methoxyethyl)acetamide was added at a rate of 1.5 g/min to a reactor maintained at a temperature of 400° C. and a pressure 20 kPaA (a tube reactor having internal a diameter of 20 mm and a length of 240 mm). A mixture of N-vinylacetamide and methanol produced by the thermal-decomposition reaction was condensed in a cooling pipe installed at an outlet of the reactor to recover the crude N-vinylacetamide. The conversion of N-(1-methoxyethyl)acetamide was 90%.

<Purification of N-Vinylacetamide>

A catalyst of 0.3% Pd—$Al_2O_3$ was packed in a column (a packed amount was set such that an amount of the catalyst was 1 ml with respect to 20 g of the crude N-vinylacetamide). The crude N-vinylacetamide was circulated at a reaction temperature of 40° C., under a hydrogen gas pressure of 0.03 MPaG, and at a SV value of 100/hr on the catalyst packed column. As a result, N-1,3-butadienylacetamide produced as a byproduct in the thermal decomposition reaction was hydrogenated and reduced. The reaction was maintained until the amount of N-1,3-butadienylacetamide reached 30 mass ppm or less. The crude N-vinylacetamide which contains a reduced amount of N-1,3-butadienylcarboxylic acid amide at a low amount was distilled under vacuum of 0.27 kPaA and at a bottom temperature of 60° C. using a simple distillation apparatus to remove methanol. The crude N-vinylacetamide was cooled and crystallized from 40° C. to 10° C. by a crystallizer to precipitate crystals of N-vinylacetamide and separated by a centrifugal separator. The crystals were washed with a liquid of methylcyclohexane:ethyl acetate=9:1, and the obtained crystals were dried. As a result, 36 g of N-vinylacetamide (a yield based on the initial acetamide was 25%) was obtained. The amount of unsaturated aldehydes in the N-vinylacetamide was 5 mass ppm or less. The results are shown in Table 2.

In the present embodiment, concentrations (concentrations after pH adjustment) of aldol and unsaturated aldehydes in the second crude N-(1-methoxyethyl)acetamide after adjusting the pH, and concentrations of aldol and unsaturated aldehyde in N-(1-methoxyethyl)acetamide after distillation were evaluated by the GC/HPLC method under the above-mentioned measurement conditions. Using these results, increasing rates in N-(1-methoxyethyl) carboxylic acid amide distillation were calculated by the following formula. The results are shown in Table 1.

[(Absolute Amount of Aldol or Unsaturated Aldehyde After Distillation)/(Absolute Amount of Aldol or Unsaturated Aldehyde Before Distillation)]×100=Increasing Rate(%)

The unsaturated aldehydes contained in N-vinylacetamide were evaluated by the GC/HPLC method under the measurement conditions described above, and the total amounts thereof are shown in Table 2.

(Polymerization Test)

Polymerization test of this embodiment was carried out as follows. A standard arrival time of the temperature peak obtained by polymerization test was 102 minutes. The results are shown in Table 2.

Here, the standard arrival time of the temperature peak was the time from the injection of the polymerization initiator to the arrival of the temperature peak.

<1> A 100 ml glass container equipped with a catalyst injection pipe, a nitrogen blowing pipe, a nitrogen exhaust pipe, and a thermometer was prepared.

<2> 20 g of N-vinylacetamide and 58 g of ion-exchanged water were weighed in the glass container of <1>.

<3> The container was heated to 30° C. with a water bath while nitrogen gas was bubbling at 50 ccm until completion of polymerization.

<4> 1.6 g of V-044 (Wako Pure Azo Imidazoline type) dissolved in 48.4 g of ion exchanged water as a polymerization initiator was added.

<5> 4.0 g of V-50 (Wako Pure Azoamidine type) dissolved 46.0 g of ion exchanged water as a polymerization initiator was added.

<6> When the nitrogen gas was passed through for 1 hour, 1 g of the polymerization initiator of <4> and 1 g of the polymerization initiator of <5> were added by using a syringe.

<7> The glass container was removed from the water bath, and water on the glass surface was removed with paper, then the container was transferred to a heat insulating container to continue the polymerization.

<8> The polymerization temperature was monitored from the addition of the polymerization initiator in <6>. The obtained standard arrival time of temperature peak was used as an indicator of polymerizability.

The standard arrival time of temperature peak of the monomer having good polymerization was set to less than 120 minutes.

Example 2

The operation was carried out in the same manner as in Example 1 except that the pH was adjusted to 8.5 in the step of adjusting the pH of N-(1-methoxyethyl)acetamide. The results are shown in Table 1 and Table 2.

Comparative Example 1

The operation was carried out in the same manner as in Example 1 except that the pH was adjusted to 7.0 in the step of adjusting the pH of N-(1-methoxyethyl)acetamide. In the purification distillation step, N-(1-methoxyethyl)acetamide did not distill out. The results are shown in Table 1 and Table 2.

Comparative Example 2

The operation was carried out in the same manner as in Example 1 except that the pH was adjusted to 9.0 in the step of adjusting the pH of N-(1-methoxyethyl)acetamide. The results are shown in Table 1 and Table 2.

Comparative Example 3

The operation was carried out in the same manner as in Example 1 except that the pH was adjusted to 10.8 in the step of adjusting the pH of N-(1-methoxyethyl)acetamide. The results are shown in Table 1 and Table 2.

Comparative Example 4

The operation was carried out in the same manner as in Example 1 except that the pH was adjusted to 12.8 in the step of adjusting the pH of N-(1-methoxyethyl)acetamide.

Table 1 shows the concentrations of aldol and unsaturated aldehydes after adjusting the pH of N-(1-methoxyethyl) acetamide, and the increasing rate after the distillation operation in each Example and Comparative Example. Table 2 shows the concentrations of the unsaturated aldehydes in the N-vinylacetamide and the results of the polymerizability test in each Example and Comparative Example. The results are shown in Table 1 and Table 2.

TABLE 1

| No. | pH | Concentration after pH Adjustment | | Increasing rate by distillation of N-(1-methoxyethyl)acetamide | |
|---|---|---|---|---|---|
| | | Aldol mass ppm | Unsaturated aldehydes mass ppm | Aldol % by mass | Unsaturated aldehydes % by mass |
| Example 1 | 8.0 | 1200 | 170 | 71.6 | 93.8 |
| Example 2 | 8.5 | 1900 | 300 | 90.3 | 126.9 |
| Com. Example 1 | 7.0 | 600 | N.D | N.D. | N.D |
| Com. Example 2 | 9.0 | 1900 | 200 | 105.2 | 201.3 |
| Com. Example 3 | 10.8 | 1800 | 160 | 117.8 | 550.2 |
| Com. Example 4 | 12.8 | 2200 | 190 | 122.9 | 790.3 |

TABLE 2

| No. | pH | Concentration of unsaturated aldehydes in N-(1-methoxyethyl)acetamide mass ppm | Standard arrival time of temperature peak in polymerization test min |
|---|---|---|---|
| Example 1 | 8.0 | <5 | 102 |
| Example 2 | 8.5 | 16 | 111 |
| Com. Example 1 | 7.0 | N.D. | N.D |
| Com. Example 2 | 9.0 | 25 | 127 |

TABLE 2-continued

| No. | pH | Concentration of unsaturated aldehydes in N-(1-methoxyethyl)acetamide mass ppm | Standard arrival time of temperature peak in polymerization test min |
|---|---|---|---|
| Com. Example 3 | 10.8 | 33 | 145 |
| Com. Example 4 | 12.8 | 57 | 189 |

INDUSTRIAL APPLICABILITY

Accordingly to the present invention, a high polymerizable N-vinylcarboxamide containing an amount of unsaturated aldehydes of 20 ppm by mass or less can be produced stably.

The invention claimed is:

1. A method of producing N-vinylcarboxylic acid amide, comprising:
   a step of obtaining N-vinylcarboxylic acid amide by using the de-alcoholization reaction from N-(1-alkoxyethyl) carboxylic acid amide,
   wherein the N-(1-alkoxyethyl) carboxylic acid amide is a compound represented by the following general formula (I),

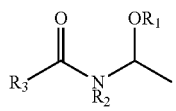

wherein $R_1$ represents an alkyl group having 1 to 5 carbon atoms, $R_2$ independently represents a hydrogen atom or an alkyl group having 1 to 5 carbon atoms, and $R_3$ represents an alkyl group having 1 to 5 carbon atoms; and
   a step of controlling an amount of unsaturated aldehydes in N-vinylcarboxylic acid amide to 20 mass ppm or less,
   wherein the step of controlling an amount of unsaturated aldehydes comprises steps of
   obtaining a second crude N-(1-alkoxyethyl) carboxylic acid amide by adjusting a pH of a first crude N-(1-alkoxyethyl) carboxylic acid amide to 8.0 to 8.5 by using 30 to 48% by mass of one selected from the group consisting of a sodium hydroxide aqueous solution and a potassium hydroxide aqueous solution; and
   purifying the N-(1-alkoxyethyl) carboxylic acid amide by distilling the second crude N-(1-alkoxyethyl) carboxylic acid amide.

2. The method of producing N-vinylcarboxylic acid amide according to claim 1, further comprising:
   a step of producing the N-(1-alkoxyethyl) carboxylic acid amide from carboxylic acid amide, acetaldehyde and alcohol; or from carboxylic acid amide and acetaldehyde dialkyl acetal.

3. The method of producing N-vinylcarboxylic acid amide according to claim 1,
   wherein the N-vinylcarboxylic acid amide is a N-vinylacetamide.

4. The method of producing N-vinylcarboxylic acid amide according to claim 1,
   wherein the unsaturated aldehydes comprises at least one selected from the group consisting of crotonaldehyde, 2-ethyl-2-butenal, 2-methyl-2-pentenal, 2-hexenal, 2,4-hexadienal, 2,4-octadienal, 2,4,6-octatrienal, and trans-2-octenal, and
   an amount of the unsaturated aldehyde is a total amount of crotonaldehyde, 2-ethyl-2-butenal, 2-methyl-2-pentenal, 2-hexenal, 2,4-hexadienal, 2, 4-octadienal, 2,4, 6-octatrienal and trans-2-octenal.

5. The method of producing N-vinylcarboxylic acid amide according to claim 1, wherein the N-vinylcarboxylic acid amide is purified by crystallization.

* * * * *